United States Patent
Petty

(10) Patent No.: US 6,651,487 B1
(45) Date of Patent: Nov. 25, 2003

(54) TEST FOR BRAKE FLUID AGE AND CONDITION

(75) Inventor: Jon A. Petty, Tucson, AZ (US)

(73) Assignee: Phoenix Systems, L.L.C., Tucson, AZ (US)

(*) Notice: Subject to any disclaimer, the term of this patent is extended or adjusted under 35 U.S.C. 154(b) by 21 days.

(21) Appl. No.: 10/030,455
(22) PCT Filed: Jul. 20, 2000
(86) PCT No.: PCT/US00/19892
§ 371 (c)(1),
(2), (4) Date: Jan. 3, 2002
(87) PCT Pub. No.: WO01/06225
PCT Pub. Date: Jan. 25, 2001

Related U.S. Application Data
(60) Provisional application No. 60/144,686, filed on Jul. 20, 1999.

(51) Int. Cl.$^7$ ................ G01N 25/08; G01N 31/32; G01D 21/00
(52) U.S. Cl. ............ 73/61.46; 73/61.77; 73/53.01; 422/82.12; 422/87; 27/57
(58) Field of Search ........ 73/61.46, 39, 53.01, 73/61.77, 61.76; 422/82.12, 61, 86, 87, 82 R; 374/16, 27, 57, 45

(56) References Cited

U.S. PATENT DOCUMENTS

| | | | |
|---|---|---|---|
| 3,081,619 A | 3/1963 | Pappas | 73/17 |
| 3,698,236 A | 10/1972 | Markey | 73/17 A |
| 3,844,159 A | 10/1974 | Mizutani | 73/17 A |
| 4,059,006 A | 11/1977 | Mizutani et al. | 73/17 A |
| 4,059,407 A * | 11/1977 | Hochstrasser | 23/253 TP |
| 4,198,207 A * | 4/1980 | Ladov et al. | 23/230 HC |
| 4,484,823 A | 11/1984 | Peuker | 374/27 |
| 4,589,277 A * | 5/1986 | Collins et al. | 73/61.1 R |
| 4,970,172 A * | 11/1990 | Kundu | 436/130 |
| 5,182,942 A * | 2/1993 | Hartel et al. | 73/61.46 |
| 5,380,091 A | 1/1995 | Buchanan | 374/16 |
| 5,433,105 A * | 7/1995 | Takahashi et al. | 73/61.46 |
| 5,518,933 A | 5/1996 | Ishibashi | 436/163 |
| 5,620,658 A * | 4/1997 | Jaunakais | 422/58 |
| 5,814,721 A | 9/1998 | Mills | 75/53.01 |
| 6,145,468 A * | 11/2000 | Woog | 116/206 |

* cited by examiner

Primary Examiner—Hezron Williams
Assistant Examiner—David Wiggins
(74) Attorney, Agent, or Firm—Antonio R. Durando; Durando Birdwell & Janke, PLC

(57) ABSTRACT

A reactive test strip having a pre-exposure color is used to measure and indicate the concentration of copper ions in brake fluid in terms of a readily visible color change. The strip is immersed in the fluid within a brake fluid container and any resulting color change is compared to a color chart and a known test standard representative of the maximum metal concentration determined empirically to correspond to a boiling point considered safe for normal operation. If the color change indicates a higher copper concentration than the known test standard, then the fluid is considered inadequate for safe operation and thus recommended for replacement without any further tests. Similar copper or metal strips can also be used in a similar test to determine iron or zinc concentration within the brake fluid so as to also determine suitability of the brake fluid for ensuring safe operation. An automated version of the reactive test strip for performing brake fluid testing includes an optical instrument to compare the color obtained during the test against a predetermined test standard and determine whether or not a brake fluid change is recommended.

27 Claims, 5 Drawing Sheets

Actual Test results using atomic plasma spectroscopy compared with test strip readings

| 0-ppm Cu | 9-ppm Cu | 30-ppm Cu | 154-ppm Cu | 365-ppm Cu |
|---|---|---|---|---|
|  |  |  |  |  |

Test Key

TEST FOR BRAKE FLUID AGE AND CONDITION

RELATED APPLICATIONS

This application is based on Provisional Application Ser. No. 60/144,686, filed Jul. 20, 1999.

BACKGROUND OF THE INVENTION

1. Field of the Invention

This invention is related in general to methods and devices for testing the efficacy of automotive brake fluid. In particular, the invention pertains to a novel approach based on a correlation between brake-fluid condition and the concentration of specific metals in the fluid, in particular copper, iron, and zinc.

2. Description of the Related Art

Brake fluid is used to transmit the pressure exerted on a motor vehicle's brake pedal to the slave cylinders of the braking system. The most commonly used brake fluids consist of glycol-based liquids categorized as DOT3 and DOT4 on the basis of the boiling point resulting from their particular composition. In order to prevent boiling of the fluid caused by overheating during use, DOT3 and DOT4 fluids are required to have a dry boiling point (with no moisture in fluid) of at least 401° F. (205° C) and 446°F. (230° C.), respectively, so that proper brake operation is ensured under all temperature conditions. A low boiling point can cause the brake fluid to vaporize under hot operating conditions, such as during continuous braking on a downhill road. Such vaporization can create pockets of compressible vapor in the system that dangerously reduce the effectiveness of the braking system. This is the occurrence normally referred to as "brake fade" which, in extreme cases, can cause complete brake failure.

All types of glycol-based brake fluid are hygroscopic. As a result of this property, they readily absorb moisture that reduces their boiling point and, if unchecked, can become dangerous. Thus, replacement of DOT3 and DOT4 fluids is desirable when they have absorbed enough moisture to decrease their vaporization temperatures to about 284° F. (140° C.) and 311° F. (155° C.), respectively, which are minimum acceptable wet boiling points (with moisture absorbed by the fluid) empirically considered safe for brake operation. Since the moisture content of brake fluid increases with age and exposure to ambient humidity, it is clear that it should be checked periodically and that the fluid should be replaced when its boiling point approaches these safety limits.

The prior art shows a variety of inventions directed to the measurement of the boiling point of brake fluid in a vehicle in order to monitor its condition. For example, U.S. Pat. No. 5,380,091 and No. 5,785,425 to Buchanan describe boiling-point sensing devices for testing fluids, in particular hydraulic fluids such as automotive brake fluid. The devices include a portable probe containing a heated chamber to receive the fluid and a thermometer adapted to measure the temperature of the vapor generated by heating the fluid. The probe is immersed either in a container filled with a sample of brake fluid or in a vehicle's brake-system reservoir to a depth sufficient to force the fluid into the chamber, where it is heated to vaporization to measure its boiling temperature.

The type of probe described in these patents has the disadvantage of requiring sampling of the fluid or access to a sufficiently deep reservoir to allow its immersion in the fluid, which is not always readily feasible. In addition, this kind of probe requires electrical power to heat the fluid to its boiling point, and at least two tests are recommended because of poor test repeatability at the relatively high temperatures of operation. Because the probes have a relatively long cycle time, in the order of 30–90 seconds, and require a cool-down time of several minutes between runs, each test is time consuming and therefore also expensive to perform. Therefore, these tests are typically not carried out for regular maintenance purposes and brake fluid is often used beyond its safe useful life.

Another approach to estimating the boiling point of brake fluid is by measuring its moisture content. Accordingly, a test strip has been developed that upon immersion in brake fluid turns to different color shades representative of the amount of water present in the fluid. One such test strip, sold by Wagner Brake Products under the trademark WETCHECK®, is currently available for this purpose, but tests have shown that it is effective only at relatively high moisture concentrations (15–20%). In addition, the different shades of color, which vary from green to light brown, are not always easily distinguishable. Therefore, this test does not provide a readily available means for monitoring the boiling point of brake fluid.

These test strips used in the art to measure moisture also suffer from the disadvantage of being unstable and subject to rapid deterioration when unprotected from ambient moisture. Unless kept in a sealed container, the strips react with moisture in the air within a matter of hours or even minutes, depending on the humidity level, and therefore soon become wasted. Moreover, after use in a test, the color of the strip continues to gradually change until the darkest shade is reached, leaving only a limited time window for accurate measurement. This shortcoming also prevents a user, such a service mechanic, from being able to show the results of a test to a customer, thereby creating an issue of credibility regarding a purported need for replacement of the fluid.

Another important aspect of brake fluids is the corrosive nature of some of their constituents, which progressively damages metallic tubing and other parts of the brake system. In conventional fluids, amines are added to inhibit corrosion and prevent damage to metal parts that operate in contact with the fluid. As the brake fluid ages, its anticorrosive properties are measured in terms of reserve alkalinity, that is, the amount of amines remaining in the fluid to buffer the acidity resulting from breakdown of fluid constituents. Over time, thermal oxidation and volatization produce a significant reduction of the amine content and the concurrent decrease of anticorrosive properties. Tests have shown that the reserve alkalinity of DOT3 and DOT4 fluids is reduced to about 20 percent of its original value after 18 to 20 months of normal operation. Therefore, brake fluids also need to be checked and periodically replaced in order to prevent dangerous corrosion in the brake system. This invention is directed at a process and a device for establishing with a simple, inexpensive test the current condition of both the boiling point and the anticorrosive properties of a brake fluid in use.

BRIEF SUMMARY OF THE INVENTION

One primary objective of this invention is a method and apparatus for determining whether the boiling point of a brake fluid in use is within allowable safety standards.

Another objective of the invention is a method and apparatus for assessing the condition of the fluid's anticorrosive properties with the same test performed to determine its boiling point.

Another goal is a test that does not require sampling of the fluid and does not involve elaborate testing procedures.

Yet another goal is a procedure that can be carried out rapidly during regular automotive maintenance.

A final objective is a procedure that can be implemented easily and economically according to the above stated criteria.

Therefore, according to these and other objectives, the preferred embodiment of the present invention consists of a reactive test strip adapted to measure and indicate the concentration of copper ions in brake fluid in terms of a readily visible color change. The strip is immersed in the fluid and the resulting color acquired by reacting with the fluid is compared to a copper concentration-versus-color chart or to a standard color representative of the maximum concentration determined empirically to correspond to a boiling point considered safe for normal operation. If the color change indicates a higher copper concentration, the brake fluid is considered inadequate for safe operation and replaced without further tests. A similar strip can also be used to determine iron concentration. An automated embodiment of the invention includes an optical instrument to compare the color obtained from the test to a predetermined standard and determine whether a fluid change is recommended.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose only some of the various ways in which the invention may be practiced.

DESCRIPTION OF THE PREFERRED EMBODIMENTS OF THE INVENTION

Figure 1:
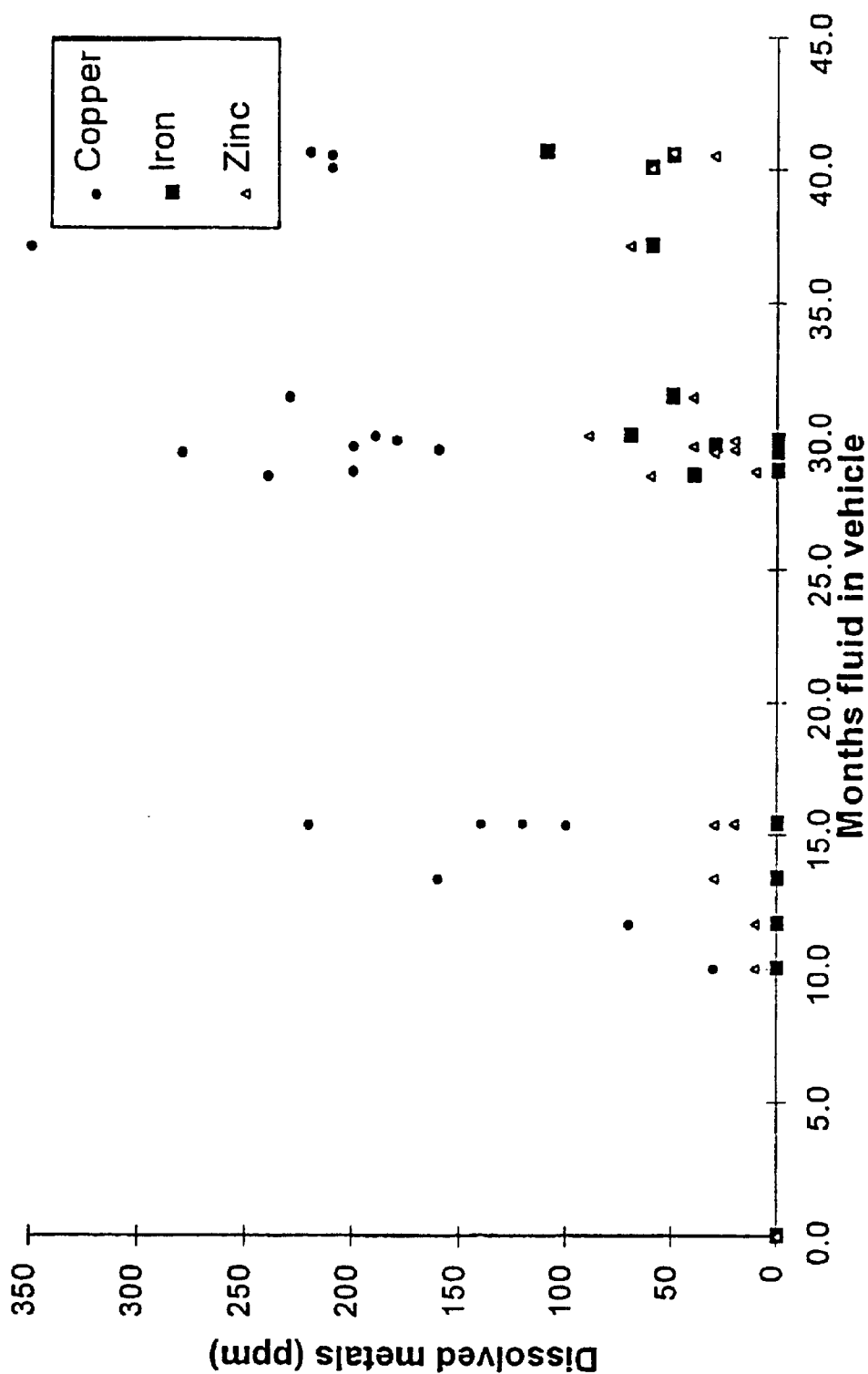
FIG. 1 is a prior-art plot showing the increase of dissolved copper, iron and zinc in commercial brake fluids as a function of time.

This invention is based on the realization that the concentration of certain metals in brake fluid increases with the age of the fluid in operation and is predictably correlated to the degradation of its boiling point and reserve alkalinity. Copper, iron and zinc are three metals commonly found in automotive brake systems. Most brake lines, which represent the highest surface area of metal in contact with brake fluid, consist of steel lined with a copper alloy. A typical light-duty vehicle uses about 14 meters of such pipe with an inside diameter of about 2.5 mm, for a total internal surface area of about 1,200 $cm^2$. Therefore, corrosion of these lines contributes relatively large amounts of copper ions to the fluid. The master and slave cylinders include steel components that are also susceptible to corrosion as the water content of the fluid increases and its reserve alkalinity decreases. Typically, dissolved iron is known to appear in the brake fluid after the initial amine corrosion inhibitor is significantly depleted and the dissolved copper level reaches about 200 ppm, as illustrated in FIG. 1.

Figure 2:
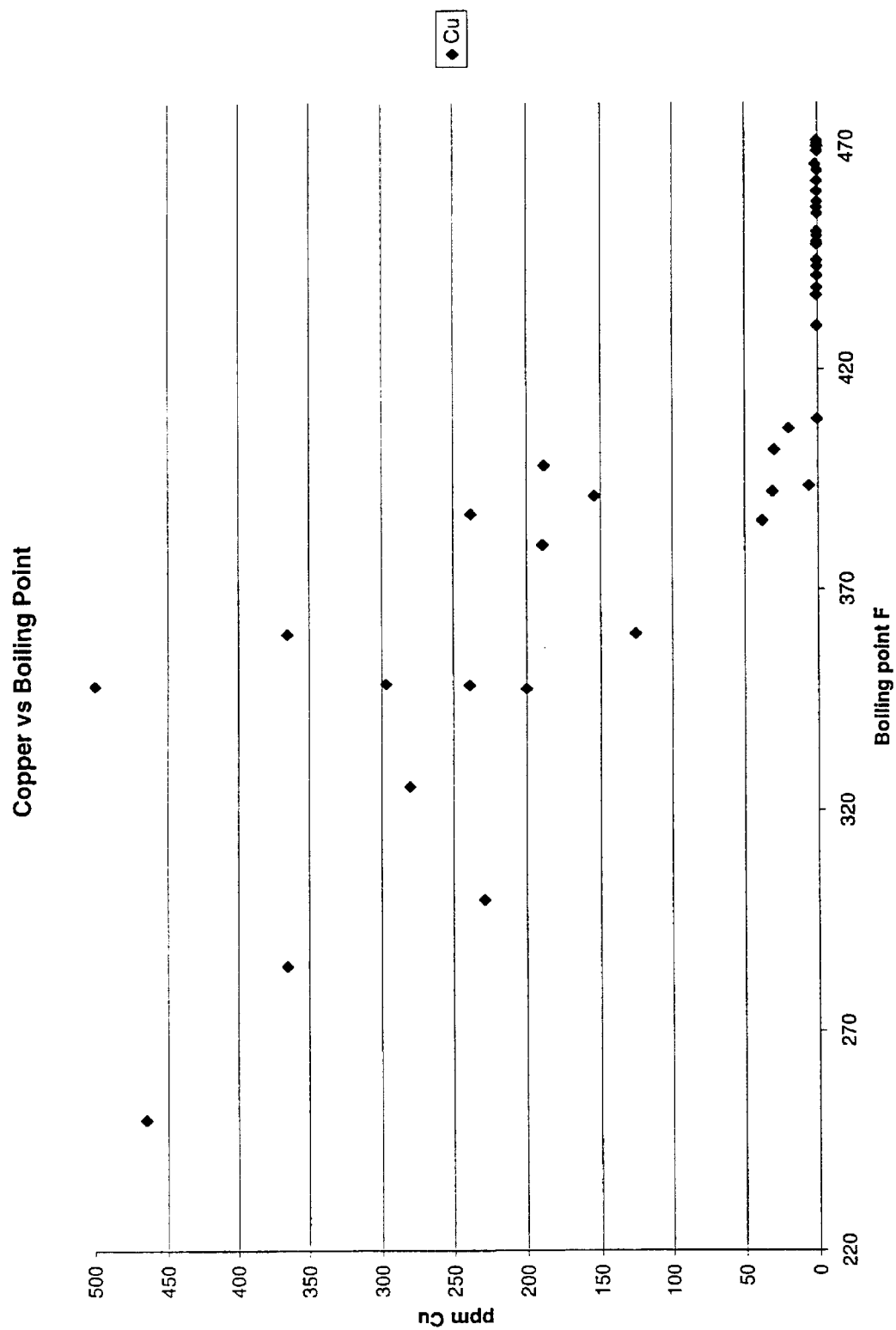
FIG. 2 is a plot showing the relationship between copper content and boiling point of commercial brake fluids.
Figure 3:
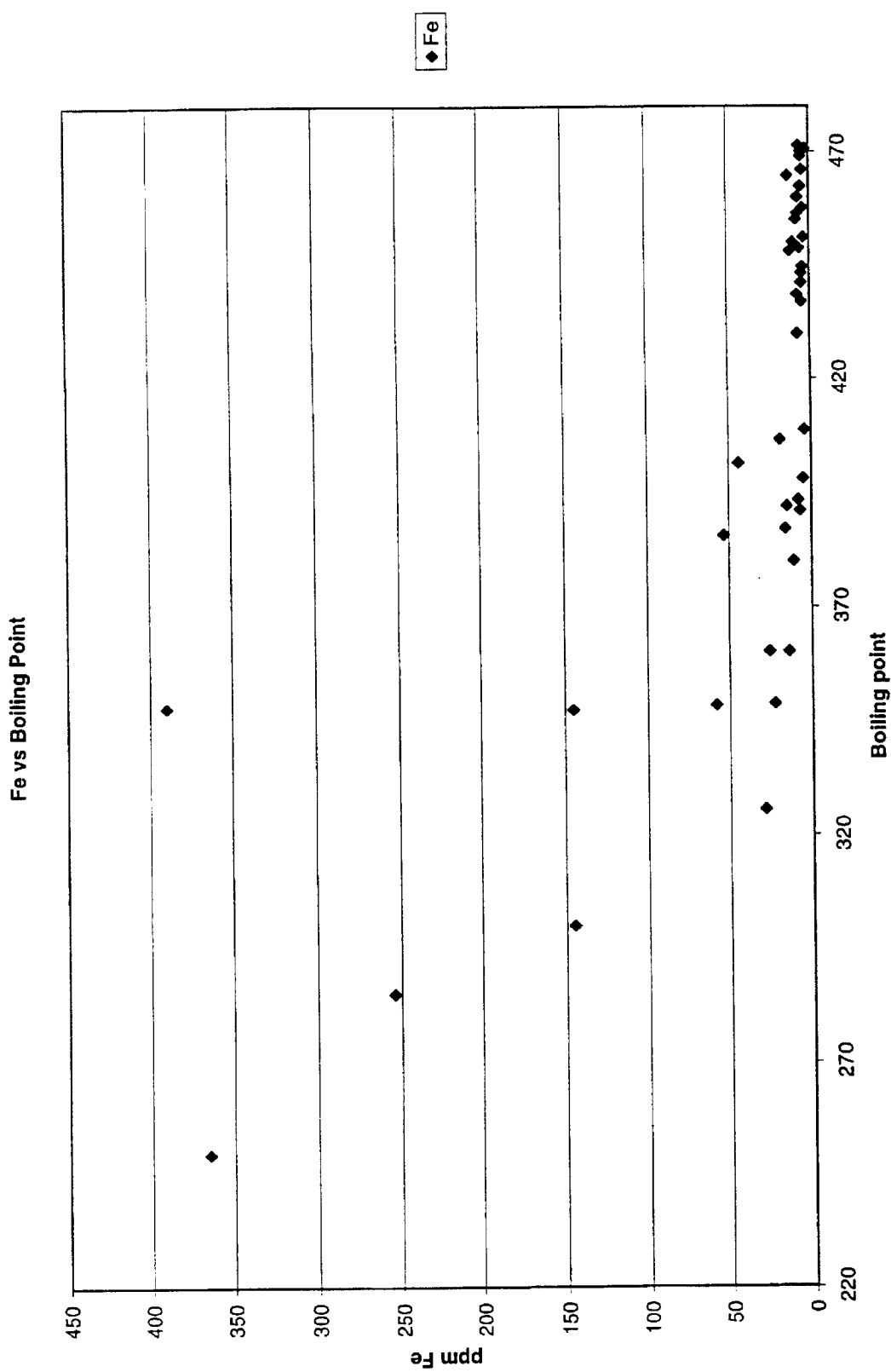
FIG. 3 is a plot showing the relationship between iron content and boiling point of commercial brake fluids.
Figure 4:
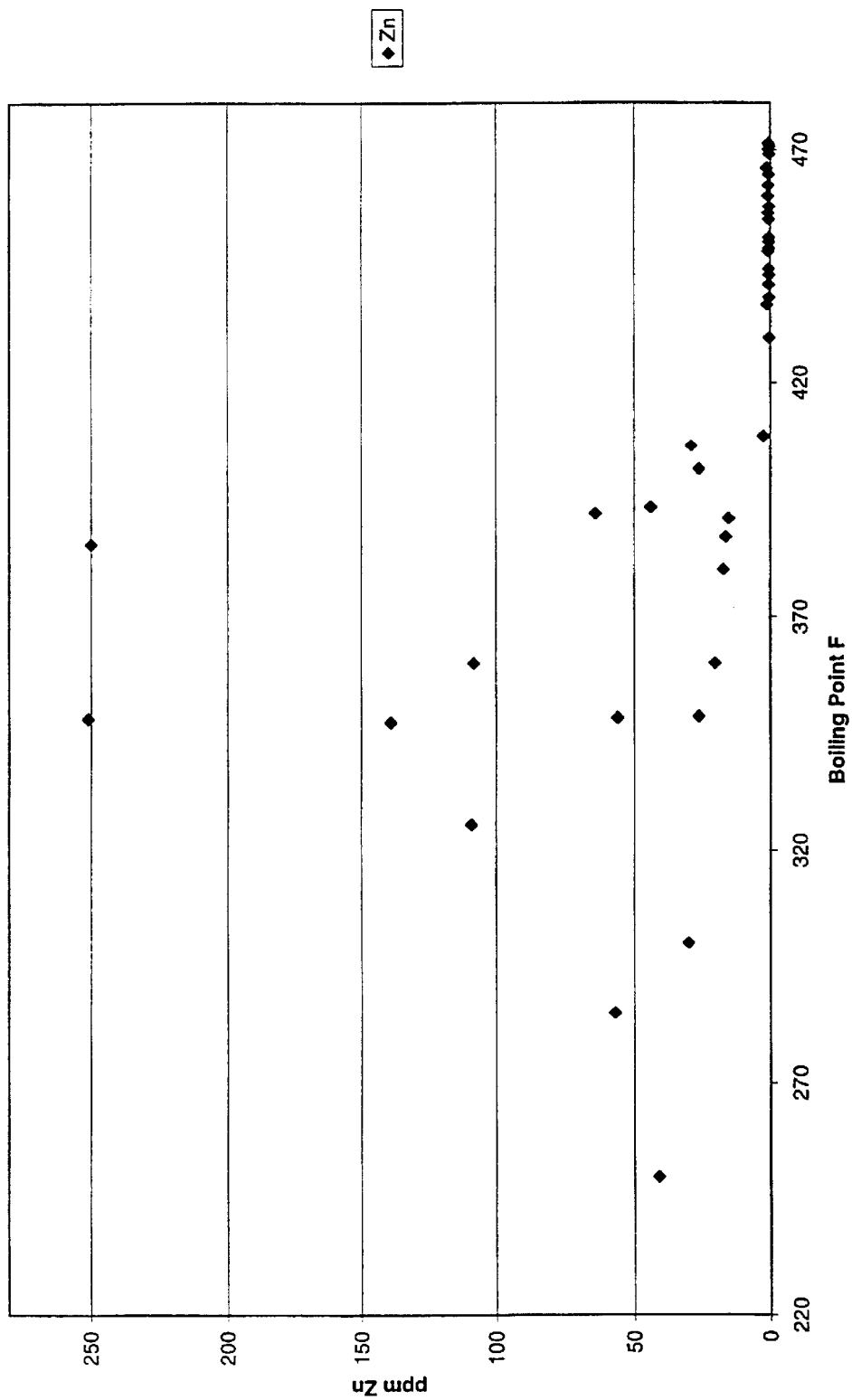
FIG. 4 is a plot showing the relationship between zinc content and boiling point of commercial brake fluids.

New DOT3 and DOT4 fluids contain about 0.5 ppm copper, 6 ppm iron, and 0.6 zinc. Since the concentration of these metals is known to increase substantially after an initial period of brake fluid operation, this invention is based on the idea of correlating metal concentrations in the fluid with boiling point and corrosiveness and utilizing metal concentration levels as indicators of the latter properties. Accordingly, the boiling point of various brake fluids was tested after different periods of operation; in addition, the concentrations of copper, iron and zinc were also measured for each sample. The two quantities (concentration and boiling point) were then plotted in graphs, illustrated in FIGS. 2–4, and shown to have a clear correlation indicating that the boiling-point temperature of all samples remained acceptable for concentrations below a certain level. For example, all samples having a copper content less than about 300 ppm showed a boiling point above the recommended minimum of 284° F. for DOT3 fluid and all those with a content less than about 150 ppm had a boiling point above the recommended minimum of 311° F. for DOT4. Similarly, all samples having an iron content less than about 150 ppm had a boiling point above the recommended minimum of 284° F., and those with a content less than about 100 ppm had a boiling point above 311°F. On the other hand, the measurements taken on zinc did not show a similarly useful correlation. (The fluids used to generate FIGS. 2–4 were undetermined mixtures of DOT3 and DOT4.)

It is noted that the brake fluids tested were sampled from vehicles in actual operation for a number of years. No differentiation was made between DOT3 and DOT4 fluids because the two are perfectly miscible (both are glycol based) and in practice they can be used interchangeably in motor vehicles, especially by drivers who choose to service their brakes themselves. Therefore, some vehicless' brake systems contain a mixture of the two after some time of operation and maintenance. Since the invention was developed to produce a test for use primarily by auto mechanics during routine maintenance of brake systems, which may include a mixture of the two types of fluids, it made sense to develop correlations that relate metal contents to the lower-temperature standard of safe operation (which in fact assumes that only DOT3 is used).

Based on these results, it became clear that a useful correlation exists between copper concentration and boiling-point temperature of brake fluids. Thus, this correlation can be used advantageously to test brake fluid because the copper content not only serves as an indicator of the degree of corrosiveness of the fluid but also provides sufficient information to determine whether or not its boiling point is still above the recommended minimum for safety purposes. The same can be stated for the iron content of the brake fluid. Accordingly, the device of the invention consists of a test strip for measuring the copper and/or iron content of the brake fluid. The strip includes a reactive component that changes color as a function of the metal concentration in the fluid. The strip is immersed in the brake fluid and allowed to react for the required amount of time to reach equilibrium;

then it is compared to a standard chart of color versus concentration to determine the current metal concentration in the fluid and its corresponding condition. If the strip color matches or surpasses the color standard corresponding to an unacceptable concentration, as determined empirically for a given metal and/or brake fluid, the fluid is assessed to be deteriorated to the point of requiring replacement. Since it is known that a relatively high concentration of copper, for example, results only after the reserve alkalinity has been depleted to the point of no longer effectively preventing corrosion, and that correspondingly the boiling point of the fluid is likely to be approaching the minimum safe level, this test can be used to readily establish maintenance requirements.

Figure 5:
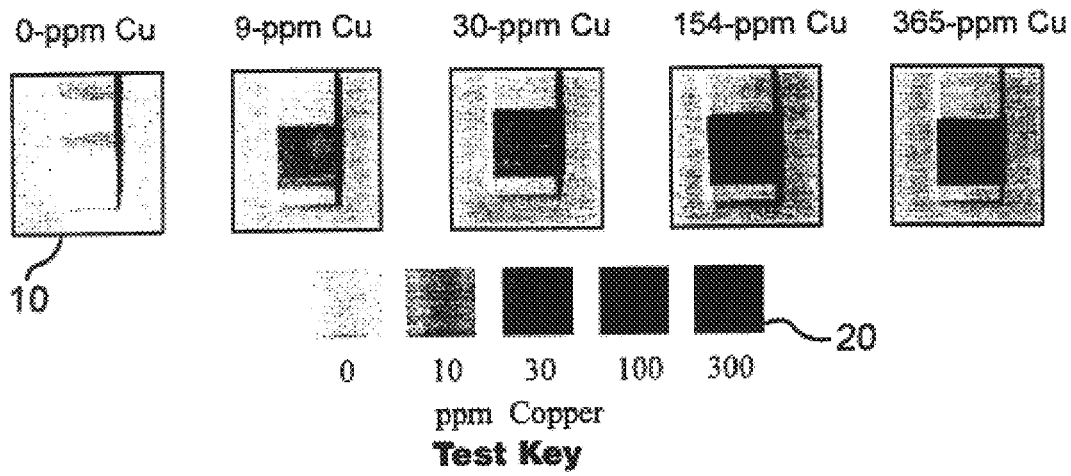
FIG. 5 is a view of the tip of the reactive strip of the invention next to a standard chart of strip color as a function of copper concentration in the brake fluid illustrating the color identification process of the invention.

Strips suitable to practice the invention are manufactured by EM Science, a division of EM Industries, Inc. For example, as illustrated in FIG. 5, the strip 10 sold as EM Quant™ varies in color from white to dark purple, with shades of increasingly dark purple corresponding to progressively higher copper concentrations ranging from 0 to 300 ppm. The color of the strip 10 is compared to a test chart 20 to determine the approximate copper concentration in the fluid. In practice, I found that a color change corresponding to a copper concentration of 150 ppm is a safe indicator of a marginal brake fluid. Experiments show that this level of dissolved copper occurs after about two years of normal use and that at that time the boiling point of the brake fluid is also consistently higher than the safe minimum of 311° F., but that it may deteriorate rapidly thereafter depending on operating conditions and the type of brake system in question. For example, antilock brake systems (ABS) include a brake-fluid recirculation circuit that fastens fluid degradation. Based on these empirical data, it was determined that 150 ppm of copper in the brake fluid would constitute an appropriate level for recommending replacement as part of regular maintenance of the brake system.

It is noted that the white-to-purple color change of copper test strips is stable and retains its shade long after the test is complete. Accordingly, the test strip can be examined for an assessment long after the test has been completed and it can be retained to show the results at a later time to a customer or other interested party. In addition, the color changes between white and purple are much more distinct and easily discernible than the variations produced by the prior-art moisture strips. These characteristics of copper strips produce more consistent results than moisture strips between tests. Finally, the copper strips are not subject to deterioration from exposure to ambient conditions. Therefore, the reactive test of the invention overcomes the noted shortcomings of the prior-art test based on moisture.

According to another aspect of the invention, an automated device could be used to compare the color change in a test strip with the standard chart of the invention. For example, a reflectometer, such as sold by EM Industries Inc. of Gibbstown, N.J., under the trademark RQflex®, can be readily utilized after calibration for the specific purpose of the invention. It includes test strips for particular metals of interest, a meter for detecting the metal concentration as a function of color change in the strip, a digital read-out, and programmable functions. The device provides quantifiable results simply by dipping a test strip in the brake fluid and then inserting it in the meter. The concentration of the metal of interest, such as copper, is read directly on a digital display. By correlating the metal concentration with the boiling point of the brake fluid according to the invention, which can be done by appropriately programming the meter, a determination of whether the fluid is still safe for use can be made rapidly and consistently according to the invention. Thus, such a device removes any subjectivity from the test. The device could also be interfaced with a computer to allow data communication for storage and printout purposes. Furthermore, a data base could be added to a computerized device to adjust the standard of comparison as a function of a vehicle's specific brake system.

Figure 6:
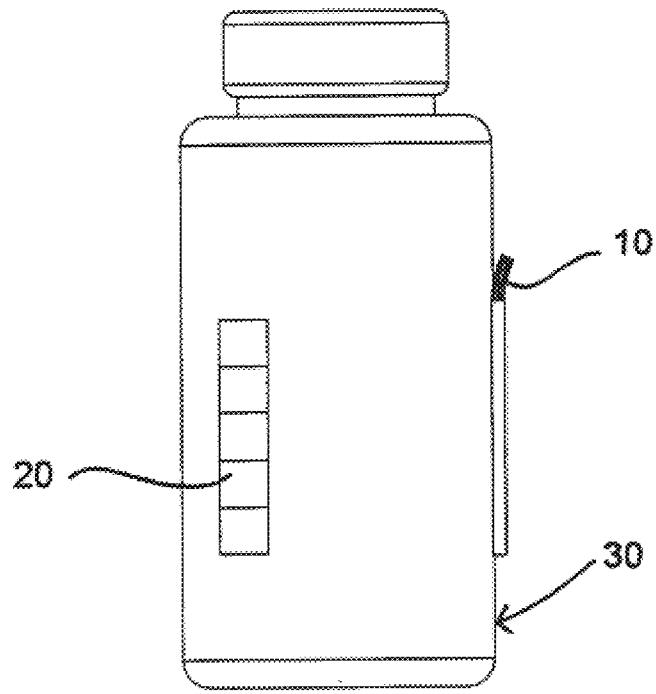
FIG. 6 is an illustration of a brake-fluid container including test strips and a color chart for testing brake fluid according to the invention.

According to another aspect of the invention, test strips could be combined with a brake fluid container 30, as illustrated in FIG. 6, to encourage testing while adding fluid for maintenance purposes. A color standard patch 20 could also be provided to conduct the test.

Thus, this invention provides an easy and accurate procedure for ascertaining the condition of brake fluid which should encourage preventive maintenance of brake systems. While it is common practice to routinely change engine oil, transmission fluid, and all filters in a vehicle, brake fluid is rarely maintained unless a malfunction occurs. This is the case even though the brake system is critical to safety and brake fluid is known to deteriorate. This invention is directed at correcting this automotive maintenance shortcoming.

The test of the invention provides the advantages of being easy to conduct because the strip produces easily discernible bright colors. The test is a good indicator of the brake fluid's age; it reveals the presence of corrosion; it shows the fluid's condition with respect to boiling point; it shows the approximate level of reserve alkalinity; and it can be performed quickly and with excellent repeatability.

Low moisture-absorption brake fluids have been introduced to the market. For example, the product sold under the trademark CASTROL GT LMA is formulated to provide low moisture activity and maintain a higher boiling point than conventional DOT3 and DOT4 brake fluids. The reactive strips of the invention were found to be advantageously suitable, subject to appropriate correlation, for testing the condition of these fluids as well.

Various changes in the details, steps and components that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

I claim:

1. A method of testing a brake fluid to determine its suitability for safe operation in a brake system as a function of the fluid's boiling-point temperature, comprising the following steps:

(a) determining a correlation between a variable indicative of a current content of a reactive constituent of the fluid and said boiling-point temperature of the fluid, where said reactive constituent is not water or moisture content in the brake fluid;

(b) measuring a current value of said variable by combining said reactive constituent with a test reactant exposed to said brake fluid;

(c) determining a current approximation of said boiling-point temperature of the fluid on the basis of the correlation between said current value and boiling-point temperature; and (d) establishing the suitability of the brake fluid for safe operation as a function of the current approximation of the fluid's boiling-point temperature on the basis of a comparison against a predetermined empirical threshold value.

2. The method of claim 1, wherein said test reactant includes a reactive strip and step (b) is carried out by immersing the strip, in the fluid and by matching a color resulting thereby on the strip with a color chart representing a correlation between color and content of said reactive constituent in the fluid.

3. The method of claim 1, wherein said reactive constituent is copper, said test reactant includes a reactive copper strip and step (b) is carried out by immersing the strip in the fluid and by matching a color resulting thereby on the strip with a color chart representing a correlation between color and copper content in the fluid.

4. The method of claim 1, wherein an automated device is used in steps (c) and (d).

5. A method of testing a brake fluid to determine its suitability for safe operation in a brake system as a function of the fluid's boiling-point temperature, comprising the following steps:

(a) determining a correlation between a variable indicative of a current content of a reactive constituent of the fluid and said boiling-point temperature of the fluid;

(b) measuring a current value of said variable by combining said reactive constituent with a test reactant exposed to said brake fluid;

(c) determining a current approximation of said boiling-point temperature of the fluid on the basis of the correlation between said current value and boiling-point temperature; and (d) establishing the suitability of the brake fluid for safe operation as a function of the current approximation of the fluid's boiling-point temperature on the basis of a comparison against a predetermined empirical threshold value;

wherein said reactive constituent is selected between the group consisting of copper and iron.

6. The method of claim 5, wherein said test reactant includes a reactive strip and step (b) is carried out by immersing the strip in the fluid and by matching a color resulting thereby on the strip with a color chart representing a correlation between color and content of said reactive constituent in the fluid.

7. The method of claim 5, wherein said reactive constituent is copper, said test reactant includes a reactive copper strip and step (b) is carried out by immersing the strip in the fluid and by matching a color resulting thereby on the strip with a color chart representing a correlation between color and copper content in the fluid.

8. The method of claim 7, wherein said current value is parts per million and said empirical threshold value is 150 ppm.

9. The method of claim 5, wherein reactive constituent is iron, said test reactant includes a reactive iron strip and step (b) is carried out by immersing the strip in the fluid and by matching a color resulting thereby on the strip with a color chart representing a correlation between color and iron content in the fluid.

10. The method of claim 9, wherein said current value is parts per million and said empirical threshold value is 100 ppm.

11. The method of claim 5, wherein an automated device is used in steps (c) and (d).

12. The method of claim 5, wherein said brake system is an automotive brake system.

13. A kit for testing a brake fluid to determine its suitability for safe operation in a brake system as a function of the fluid's boiling-point temperature, where said reactive constituent is not water or moisture content in the brake fluid, comprising:

a test standard representing a correlation between a content of a reactive constituent in the fluid and said boiling-point temperature;

a test reactant capable of reacting with the reactive constituent in the fluid upon exposure of said test reactant with said brake fluid and producing an indication of a current content of the reactive constituent in the fluid; and a predetermined empirical threshold value to be used for comparison purposes in establishing the suitability of the brake fluid for safe operation as a function of said current content of the reactive constituent in the fluid.

14. The kit of claim 13, wherein said test reactant includes a reactive strip adapted for immersion in the fluid to produce said indication of a current content of the reactive constituent in the fluid.

15. The kit of claim 13 wherein said reactive constituent is copper, said test reactant includes a reactive copper strip, and said test standard includes a copper color chart.

16. The kit of claim 13, further comprising an automated device for producing said indication of a current content of the reactive constituent in the fluid, and for establishing the suitability of the brake fluid for safe operation as a function of said current content of the reactive constituent in the fluid.

17. A kit for testing a brake fluid to determine its suitability for safe operation in a brake system as a function of the fluid's boiling-point temperature, comprising:

a test standard representing a correlation between a content of a reactive constituent in the fluid and said boiling-point temperature;

a test reactant capable of reacting with the reactive constituent in the fluid upon exposure of said test reactant with said brake fluid and producing an indication of a current content of the reactive constituent in the fluid; and a predetermined empirical threshold value to be used for comparison purposes in establishing the suitability of the brake fluid for safe operation as a function of said current content of the reactive constituent in the fluid;

wherein said reactive constituent is selected between the group consisting of copper and iron and said test standard includes a color chart.

18. The kit of claim 17 wherein said reactive constituent is copper, said test reactant includes a reactive copper strip, and said test standard includes a copper color chart.

19. The kit of claim 18, wherein said indication of a current content of the reactive constituent in the fluid is parts per million and said empirical threshold is 150 ppm.

20. The kit of claim 17, wherein said reactive constituent is iron, said test reactant includes a reactive iron strip, and said test standard includes an iron color chart.

21. The kit of claim 20, wherein said indication of a current content of the reactive constituent in the fluid is parts per million and said empirical threshold is 100 ppm.

22. The kit of claim 17, wherein said test reactant includes a reactive strip adapted for immersion in the fluid to produce said indication of a current content of the reactive constituent in the fluid.

23. The kit of claim 17, further comprising an automated device for producing said indication of a current content of the reactive constituent in the fluid, and for establishing the suitability of the brake fluid for safe operation as a function of said current content of the reactive constituent in the fluid.

24. A brake-fluid-dispenser and test kit comprising:
    a container with brake fluid;
    a test standard representing a correlation between a content of a reactive constituent in the fluid and a boiling-point temperature of the fluid, where said reactive constituent is not water or moisture content in the brake fluid; and
    a test reactant capable of reacting with the reactive constituent in the fluid and producing an indication of a current content of the reactive constituent in the fluid upon exposure of said test reactant with said brake fluid, including a predetermined empirical threshold value to be used for comparison purposes in establishing the suitability of the brake fluid for safe operation as a function of said current content of the reactive constituent in the fluid.

25. The kit of claim 24, wherein said test reactant includes a reactive strip adapted for immersion in the fluid to produce said indication of a current content of the reactive constituent in the fluid.

26. A brake-fluid dispenser and test kit comprising:
    a container with brake fluid;
    a test standard representing a correlation between a content of a reactive constituent in the fluid and a boiling-point: temperature of the fluid; and
    a test reactant capable of reacting with the reactive constituent in the fluid and producing an indication of a current's content of the reactive constituent in the fluid upon exposure of said test reactant with said brake fluid, including a predetermined empirical threshold value to be used for comparison purposes in establishing the suitability of the brake fluid for safe operation as a function of said current content of the reactive constituent in the fluid;
    wherein said reactive constituent is selected between the's group consisting of copper and iron and said test standard includes color chart.

27. The kit of claim 26, wherein said test reactant includes a reactive strip adapted for immersion in the fluid to produce said indication of a current content of the reactive constituent in the fluid.

* * * * *

UNITED STATES PATENT AND TRADEMARK OFFICE
CERTIFICATE OF CORRECTION

PATENT NO. : 6,651,487 B1
DATED : November 25, 2003
INVENTOR(S) : Jon A. Petty

It is certified that error appears in the above-identified patent and that said Letters Patent is hereby corrected as shown below:

Column 7,
Line 6, delete "," after "strip"

Column 10,
Line 8, replace "current's" with -- current --
Line 15, replace "the's" with -- the --
Line 17, add -- a -- after "includes"

Signed and Sealed this

Eighteenth Day of May, 2004

JON W. DUDAS
*Acting Director of the United States Patent and Trademark Office*